US006238898B1

(12) United States Patent
Häusler et al.

(10) Patent No.: US 6,238,898 B1
(45) Date of Patent: May 29, 2001

(54) HYDROPEROXIDE LYASES

(75) Inventors: Alex Häusler, Schwerzenbach; Konrad Lerch, Pfaffhausen; Andreas Muheim; Natasha Silke, both of Zürich, all of (CH)

(73) Assignee: Givaudan Roure (International) SA, Vernier-Geneve (CH)

( * ) Notice: Subject to any disclaimer, the term of this patent is extended or adjusted under 35 U.S.C. 154(b) by 0 days.

(21) Appl. No.: 09/418,222

(22) Filed: Oct. 14, 1999

Related U.S. Application Data

(62) Division of application No. 08/833,553, filed on Apr. 7, 1997, now Pat. No. 6,008,034.

(30) Foreign Application Priority Data

Apr. 15, 1996 (EP) .................................................. 96105856
Sep. 25, 1996 (EP) .................................................. 96115335

(51) Int. Cl.⁷ .................................. C12P 7/02; C12P 7/04
(52) U.S. Cl. .......................... 435/155; 435/157; 435/232; 435/252.33; 435/254.11; 435/254.21; 536/23.2
(58) Field of Search .................................. 435/132, 157, 435/155, 232, 252.3, 252.33, 320, 254.11, 254.21; 536/23.2

(56) References Cited

U.S. PATENT DOCUMENTS 5,047,513   9/1991   Dobeli et al. .................. 530/412
5,620,879 * 4/1997   Brunerie et al. .................. 435/155

FOREIGN PATENT DOCUMENTS 0 253 303   1/1988   (EP) .
0 282 042   9/1988   (EP) .

OTHER PUBLICATIONS

Matsui et al. "Fatty acid hydroperoxide cleaving enzyme, hydroperoxide lyase, from tea leaves" Phytochemistry 30, 2109–2113, 1991.*
Kim et al. "Partial purification and properties of a hydroperoxide lyase from fruits of pear" J. Agric. Food Chem. 29, 1220–1225, 1981.*
Uritani et al. "Odor compounds produced in peel of mature–green banana fruit" Postharvest Biochemistry of Plant Food--Materials in the Tropics, (Uritani et al. Eds.)pp. 193–201, Japan Science Press, Tokyo, Japan, 1994.*
Berger et al. "Methods in Enzymol.: Guide to Molecular Cloning Techniques" vol. 152, pp. 393–399, 415–423, 432–447, and 661–705, 1987.*

SIGMA Chemical Compony Cataloug, pp. 190 and 677, 1988.*
Orlean et al. *Methods in Enzymology*, Gunthrie & Fink, eds., vol. 194:682–697 (1991).
Mylin, L.M., et al., *Methods in Enzymology*, vol. 185:297–308, (1991).
Sherman, F., *Methods in Enzymology*, vol. 194:3–21, (1991).
Sagi, L., et al., *Bio/Technology*, vol. 13:481–485, (1995).
Luckow, V.A., et al., *Bio/Technology*, vol. 6:47–55, (1988).
Charm, S.E., et al., *Methods in Enzymology*, vol. 22:476–556, (1971).
Hochuli, E., et al., *Biol. Chem. Hoope–Seyler*, vol. 368:748, (1987).
Romanos, M.A., et al. *Yeast*, vol. 8:423–488, (1992).
Grunstein, M., et al., *Proc. Nat. Acad. Sci. USA*, vol. 72(10):3961–3965, (1975).
Smith, G.E., et al., *Proc. Nat. Acad. Sci. USA*, vol. 82:8404–8408, (1985).
Christou, P., et al., *TibTech*, vol. 8:145–151, (1990).
Klebe, R.J., et al., *Gene*, vol. 25:333–341, (1983).
Dong, J.Z., et al., *Plant Science*, vol. 88:61–71, (1993).
Villarejo, M.R., et al., *J. Bacteriol.*, vol. 120:466–474, (1974).
May, G.D., et al., *Bio/Technology*, vol. 13:486–492, (1995).
Bujard, H., et al., *Methods in Enzymology*, vol. 155:416–433, (1987).
Olias, J.M., et al., *J. Agric. Food. Chem.*, vol. 41:2368–2373, (1993).
Iacazio, G., et al., *J. Org. Chem.*, vol. 55:1690–1691 (1990).
Benton, W.D., et al., *Science*, vol. 196:180–182, (1977).
Ishida, Y., et al., *Nature Biotechnology*, vol. 14:745–750, (1996).
Kilsby, D.C., *Int. J. Food and Microbiol.*, vol. 50:59–63, (1999).

* cited by examiner

Primary Examiner—Nashaat T. Nashed
(74) Attorney, Agent, or Firm—Mark E. Waddell; Stephen M. Haracz; Bryan Cave LLP

(57) ABSTRACT

The present invention relates to the production of HPO lyase proteins in hosts via recombinant expression of said proteins. Recombinant HPO lyase proteins, DNA sequences encoding these proteins, vectors containing these DNA sequences and hosts containing these vectors are provided, along with methods for recombinantly producing such proteins, DNA sequences, vectors and hosts. Also provided are processes for producing green note compounds.

2 Claims, 2 Drawing Sheets

US 6,238,898 B1

HYDROPEROXIDE LYASES

This is a divisional of application Ser. No. 08/833,553 filed on Apr. 7, 1997 now U.S. Pat. No. 6,008,034.

FIELD OF THE INVENTION

The present invention relates to hydroperoxide lyases (hereinafter also referred to as HPO lyase proteins or proteins with HPO lyase activity), their microbial production via recombinant DNA technology, and their use for the production of aliphatic aldehydes and alcohols, flavor molecules known as "green notes".

BACKGROUND OF THE INVENTION

"Green notes" are volatile flavor and fragrance molecules present in a wide variety of plant leaves, vegetables and fruits characterized in organoleptic terms as fresh "green" and grassy. These compounds are produced by the plant from the degradation of unsaturated fatty acids (linoleic and linolenic acid). In FIG. 1 the formation of a variety of linolenic acid degradation products is summarized.

Degradation of polyunsaturated fatty acids starts by the oxygenation at cis—cis double bonds of polyunsaturated fatty acids. This reaction is catalyzed by lipoxygenase (EC 1.13.11.12)-enzymes which are present in plants, animals and microorganisms. The oxygenated products, fatty acid hydroperoxides, are precursors for many important hormones (e.g. prostaglandins, lipoxins, jasmonic acid, traumatic acid) and flavor/fragrance molecules (e.g., cis-3-hexenol, 1-octen-3-ol). In plants, cleavage of the hydroperoxides occurs through the action of specific hydroperoxide lyases.

Commercial production of natural "green note" compounds is currently achieved by fractional distillation of essential oils such as mint oil or by the combined action of lipoxygenase and hydroperoxide lyase on unsaturated fatty acids using plant material from different sources.

However, these processes have the drawbacks that they provide low yields and/or depend on specific plant materials.

SUMMARY OF THE INVENTION

It has now been found that high reproducible yields of "green note" compounds (e.g., cis-3-hexenol) can be obtained independent of plant materials and in the absence of unwanted side reaction (e.g. isomerase activity) by transfer of the gene coding for HPO lyase from plant into host cells, subsequent expression of the gene, addition of linolenic acid hydroperoxide as substrate, and reduction of cleaved substrate by aldehyde dehydrogenase. In FIG. 2 the formation of cis-3-hexenol from 13-(S)-hydroperoxy linolenic acid by recombinant HPO lyase is summarized.

Thus, in a first aspect of this invention, there are provided isolated DNA sequences encoding proteins with HPO lyase activity or fragments thereof. Specifically, the DNA sequences of this invention are defined to include the nucleotide sequence SEQ ID No:1 or a fragment thereof or any DNA sequence which is substantially homologous to the nucleotide sequence SEQ ID No:1 or a fragment thereof.

As used hereinbefore the term "substantially homologous", means that a particular subject sequence, for example, a mutant sequence, varies from a reference sequence by one or more substitutions, deletions, or additions, the net effect of which does not result in an adverse functional dissimilarity between the reference and subject sequences. For purposes of the present invention, DNA sequences having greater than 95 percent homology, encoding equivalent biological properties, and showing equivalent expression characteristics are considered substantially homologous. For purposes of determining homology, truncation of the DNA sequence should be disregarded. Sequences having lesser degrees of homology, encoding comparable bioactivity, and showing equivalent expression characteristics, e.g., fragments of the nucleotide sequence SEQ ID No:1 are considered substantial equivalents. Generally, homologous DNA sequences can be identified by cross-hybridization under standard hybridization conditions of moderate stringency.

There are also provided vectors and expression vectors containing the DNA sequences of the present invention, hosts containing such vectors for the production of proteins with HPO lyase activity, and processes for the production of such DNA sequences, recombinant vectors and host cells.

There are further provided recombinant proteins with HPO lyase activity. Specifically a protein with HPO lyase activity is defined to include the amino acid sequence SEQ ID No:2 or any protein or polypeptide having an amino acid sequence which is substantially homologous to the amino acid sequence SEQ ID No:2 and further having the following biological activity: When the protein or polypeptide is incubated under suitable conditions and a suitable amount of substrate such as 13-(S)-linolenic acid hydroperoxide is added, the formation of cis-3-hexenal is observed.

As used hereinbefore the term "substantially homologous" means that a particular subject sequence, for example, a mutant sequence, varies from a reference sequence by one or more substitutions, deletions, or additions, the net effect of which does not result in an adverse functional dissimilarity between the reference and subject sequences. For purposes of the present invention, sequences having greater than 95 percent homology, equivalent biological activity and equivalent expression characteristics are considered substantially homologous. For purposes of determining homology, truncation of the sequence should be disregarded. Sequences having lesser degrees of homology, comparable bioactivity, and equivalent expression characteristics, e.g., fragments of the amino acid sequence SEQ ID No:2 are considered substantial equivalents.

As used herein the term recombinant proteins with HPO lyase activity includes proteins modified deliberately, as for example, by addition of specific sequences that preferably bind to an affinity carrier material. Examples of such sequences are sequences containing at least two adjacent histidine residues (see in this respect European Patent No. 282 042). Such sequences bind selectively to nitrilotriacetic acid nickel chelate resins (Hochuli and Döbeli, Biol. Chem. Hoope-Seyler 368, 748 (1987); European Patent No. 253 303). Proteins with HPO lyase activity which contain such a specific sequence can, therefore, be separated selectively from the remaining polypeptides. The specific sequence can be linked either to the C-terminus or the N-terminus of the proteins with HPO lyase activity.

Methods for the expression, isolation and purification of the proteins with HPO lyase activity are also provided.

The following steps outline the methods for recombinantly expressing the proteins with HPO lyase activity.

1) Cloning of DNA sequences encoding proteins with HPO lyase activity

DNA sequences encoding proteins with HPO lyase activity can be cloned using a variety of techniques. Using the methods described in this application cDNAs encoding proteins with HPO lyase activity or fragments thereof can be produced. These cDNAs can be isolated and amplified by PCR technique using oligodeoxynucleotide DNA primers by conventional techniques.

The cDNA (SEQ ID No:1) encoding the amino acid sequence SEQ ID No:2 is obtained using the DNA primers described in the examples. By using conventional technique, this cDNA has been isolated from a lambda phage cDNA library made from RNA derived from banana (Musa sp.) leaves.

The cDNA may be obtained not only from cDNA libraries, but by other conventional techniques, e.g., by cloning genomic DNA, or fragments thereof, purified from the desired cells. These procedures are described by Sambrook et al., in "DNA Cloning: A Practical Approach", Vol. I and II, D. N. Glover, ed., 1985, MRL Press, Ltd., Oxford, U. K; Benton and Davis, Science 196, 180–182 (1977); and Grunstein and Hogness, Proc. Nat. Acad. Sci. 72, 3961–3965 (1975).

To obtain the cDNA encoding the proteins with HPO lyase activity cDNA libraries are screened by conventional DNA hybridization techniques by the methods of Benton and Davis, supra, or Grunstein and Hogness, supra, using radioactive HPO lyase gene fragments. Clones which hybridize to the radioactive gene fragments are analyzed, e.g., by restriction endonuclease cleavage or agarose gel electrophoresis. After isolating several positive clones the positive insert of one clone is subcloned, e.g., into phagemids, and sequenced by conventional techniques.

Clones derived from genomic DNA may contain regulatory and intron DNA regions in addition to coding regions; clones derived from cDNA will not contain intron sequences. In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Whatever the source, the DNA sequence encoding proteins with HPO lyase activity may be molecularly cloned into a suitable vector for propagation of the DNA by methods known in the art. Any commercially available vector may be used. For example, the DNA may be inserted into a pBluescript SK vector. Appropriate vectors for use with bacterial hosts are described by Pouwels et al., in "Cloning Vectors: A Laboratory Manual", 1985, Elsevier, N.Y. As a representative but nonlimiting example, useful cloning vectors for bacterial use can comprise a selectable marker and a bacterial origin of replication derived from commercially available plasmids which are in turn derived from the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA).

The DNA sequences encoding proteins with HPO activity inserted in these commercially available vectors can be verified by methods known in the art, e.g., by standard nucleotide sequencing techniques.

DNA sequences that code for proteins with HPO activity from plants other than banana may be used herein. Accordingly, while specific DNA has been cloned and sequenced in relation to the DNA sequence in banana leaves, any plant cell potentially can be used as the nucleic acid source of the protein with HPO activity.

2) Production of proteins with HPO lyase activity

Cloned DNA sequences that code for proteins with HPO lyase activity can be expressed in hosts to enable the production of these proteins with greater efficiency. Techniques for these genetic manipulations are specific for the different available hosts and are known in the art.

For expression of proteins with HPO lyase activity in hosts, in principle, all vectors which replicate and express DNA sequences encoding the proteins with HPO lyase activity in the chosen host are suitable. Expression vectors suitable for use in prokaryotic host cells are mentioned, for example, in the textbook "Molecular Cloning—A Laboratory Manual", Cold Spring Harbor Laboratory (1982), of Maniatis et al. Examples of other vectors are plasmids of the pDS family [Bujard et al., Methods in Enzymology, eds. Wu and Grossmann, Academic Press, Inc., Vol. 155, 416–433 (1987)].

Such prokaryotic expression vectors which contain the DNA sequences coding for the proteins with HPO lyase activity operatively linked with an expression control sequence can be incorporated using conventional methods into any suitable prokaryotic host cell. The selection of a suitable prokaryotic host cell is determined by different factors which are well-known in the art. Thus, for example, compatibility with the chosen vector, toxicity of the expression product, expression characteristics, necessary biological safety precautions and costs play a role and a compromise between all of these factors must be found.

Suitable prokaryotic host organisms include gram-negative and gram-positive bacteria, for example *E. coli* and *B. subtilis* strains. Examples of prokaryotic host organisms are *E. coli* strain M15 (described as strain OZ 291 by Villarejo et al. in J. Bacteriol. 120, 466–474 [1974] and *E. coli* W3110 [ATCC No. 27325]). In addition to the aforementioned *E. coli* strains, however, other generally accessible *E. coli* strains such as *E. coli* 294 (ATCC No. 31446) and *E. coli* RR1 (ATCC No. 31343) can also be used.

In a preferred embodiment of the present invention yeast is used as the host organism. Expression vectors suitable for use in yeast cells are described in "Guide to yeast genetics and molecular biology", Guthrie and Fink, eds., Methods in Enzymology, Academic Press, Inc., Vol. 194 (1991) and "Gene expression technology", Goeddel, ed., Methods in Enzymology, Academic Press, Inc., Vol. 185 (1991). The preferred yeast vector of the present invention is the plasmid pYX233 (R&D systems, Abingdon, UK). Examples of suitable yeast cells are *Saccharomyces cerevisiae, Pichia pastoris, Hansenula polymorpha, Schizosaccharomyces pombe* cells. An overview on various yeast expression systems is given by Romanos et al., Yeast, Vol. 8, 423–488 (1992). Especially preferred yeast cells of the present invention are *S. cerevisiae* DBY746 [ATCC 44773].

The transformation with the yeast expression vectors is carried out as described by Klebe et al., Gene, Vol. 25, 333–341 (1983).

The manner in which the expression of the proteins with HPO lyase activity is carried out depends on the chosen expression vector host cell system.

Usually, the prokaryotic host cells which contain a desired expression vector are grown under conditions which are optimal for the growth of the prokaryotic host cells. At the end of the exponential growth, when the increase in cell number per unit time decreases, the expression of the desired protein with HPO lyase activity is induced, i.e., the DNA coding for the desired protein with HPO lyase activity is transcribed and the transcribed mRNA is translated. The induction can be carried out by adding an inducer or a derepressor to the growth medium or by altering a physical parameter, e.g., a change in temperature. For example, the expression can be controlled by the lac repressor.

By adding isopropyl-β-D-thiogalactopyranoside (IPTG), the expression control sequence is derepressed and the synthesis of the desired protein is thereby induced.

The yeast host cells which contain a desired expression vector are grown under conditions which are optimal for the growth of the yeast host cells. A typical expression vector contains the promoter element, which mediates the transcription of mRNA, the protein coding sequence, a ribosomal binding site for effective translation. Additional elements may include terminator, signal, and upstream activating sequences.

The yeast cells are grown as described by Sherman in "Guide to yeast genetics and molecular biology", Guthrie and Fink, eds., Methods in Enzymology, Academic Press, Inc., Vol. 194, 3–21 (1991).

The baculovirus-insect cell vector system can also be used for the production of the proteins with HPO lyase activity of the present invention (for review see Luclow and Summers, Bio Technology 6, 47–55 [1988]). The proteins with HPO lyase activity produced in insect cells infected with recombinant baculovirus can undergo post-translational processing including N-glycosylation (Smith et al., Proc. Nat. Scad. Sci. USA 82, 8404–8408) and O-glycosylation (Thomsen et al., 12. International Herpesvirus Workshop, University of Philadelphia, Pa.).

Plants can also be used as hosts for the recombinant production of proteins with HPO lyase activity. Transfer of the gene coding for the protein with HPO lyase activity may be achieved by a variety of methods (for review see Potrykus and Spangenberg, eds., Gene transfer to plants. A laboratory manual, Springer Verlag, Heidelberg, Germany (1995)), whereby the HPO lyase gene is integrated into the chromosome of the host plant. Homologous expression—overexpression—of the protein with HPO lyase activity can be achieved, for example, by transforming a banana (Musa sp.) plant with the HPO lyase gene isolated from a banana gene library. A transformation protocol of banana plants can be found in Bio Technology 13 (5), 486–492 (1995) or Bio Technology 13 (5), 481–485 (1995). Other examples for plant hosts for the production of recombinant HPO lyase protein include, but are not limited to maize (*Zea mays*, Ishida et al., Nature Biotechnology 14, 745–750 (1996)), flax (*Linum usitatissimum*, Dong and Mchughen, Plant Sci. 88 (1), 61–71 (1993)) and soybean (*Glycine max*, Christou et al., Tibtech 8, 145–151 (1990)).

For the isolation of small amounts of proteins with HPO lyase activity expressed in prokaryotic host cells for analytical purposes, e.g., for polyacrylamide gel electrophoresis, the host cells can be disrupted by treatment with a detergent, e.g., sodium dodecyl sulphate (SDS). Larger quantities of the HPO lyase protein can be obtained by mechanical [Charm et al., Meth. Enzymol. 22, 476–556 (1971)], enzymatic (lysozyme treatment) or chemical (detergent treatment, urea or guanidinium hydrochloride treatment, etc.) treatments followed by use of known methods, e.g., by centrifugation at different gravities, precipitation with ammonium sulphate, dialysis (at normal pressure or at reduced pressure), preparative isoelectric focusing, preparative gel electrophoresis or by various chromatographic methods such as gel filtration, high performance liquid chromatography (HPLC), ion exchange chromatography, reverse phase chromatography and affinity chromatography (e.g., on Sepharose® Blue CL-6B).

For the isolation of small amounts of proteins with HPO lyase activity expressed in yeast host cells for analytical purposes, e.g., for polyacrylamide gel electrophoresis, the host-cells can be disrupted by the use of glass beads as described by Orlean et al. in "Guide to yeast genetics and molecular biology", Guthrie and Fink, eds., Methods in Enzymology, Academic Press, Inc., Vol. 194, 682–697 (1991). Larger quantities of the proteins with HPO lyase activity can be obtained by passing recombinant yeast cells through a Dyno-Mill apparatus filled with glass beads according to the instructions of the manufacturer (Willy Bachofen, Maschinenfabrik AG, Basel, Switzerland).

The proteins with HPO lyase activity expressed in the baculovirus-insect cell vector system can be isolated from the host cell medium using standard protein purification methods.

The proteins with HPO lyase activity can be used in the production of natural "green note" compounds by catalyzing the formation of aldehydes from fatty acid hydroperoxide.

Hence the present invention also provides a process for the production of natural "green note" compounds, which process comprises the steps of:
a) reacting fatty acid hydroperoxide in the presence of recombinant proteins with HPO lyase activity; and
b) reacting the resulting aliphatic aldehydes in the presence of isomerase and/or alcohol dehydrogenase.

The term "green note" compounds relates to leaf aliphatic aldehydes and leaf aliphatic alcohols, e.g., cis-3-hexenol and trans-2-hexenal. Examples of fatty acid hydroperoxides are given in FIG. 1.

In the process for the production of natural "green note" compounds the proteins with HPO lyase activity can be used in isolated form, or alternatively, in form of cell-free extracts obtained from host cells containing vectors for the production of protein with HPO lyase activity.

In a preferred specific embodiment of the present invention, the process for the production of natural "green note" compounds is employed to produce cis-3-hexenol. The specific process for producing cis-3-hexenol comprises the steps of:
a) reacting 13-(S)-hydroperoxide linolenic acid in the presence recombinant proteins with HPO lyase activity; and
b) reducing the resulting cis-3-hexanal with alcohol dehydrogenase.

In performing the specific process for producing cis-3-hexenol, preferably the proteins with HPO lyase activity are obtained from *Saccharomyces cerevisiae* cells containing vectors for the production of said proteins and reduction of cis-3-hexenal to cis-3-hexenol is catalyzed be endogeneous aldehyde dehydrogenase. FIG. 2 summarizes schematically this specific process.

The green note compounds, e.g. cis-3-hexenol, prepared by the process of the present invention can be used as odorant and/or flavorant and worked into odorant and/or flavorant compositions in a manner known per se.

Having now generally described this invention, the same will become better understood by reference to the specific examples, which are included herein for purpose of illustration only and are not intended to be limiting unless otherwise specified, in connection with the following figures:

DETAILED DESCRIPTION

Figure 1:
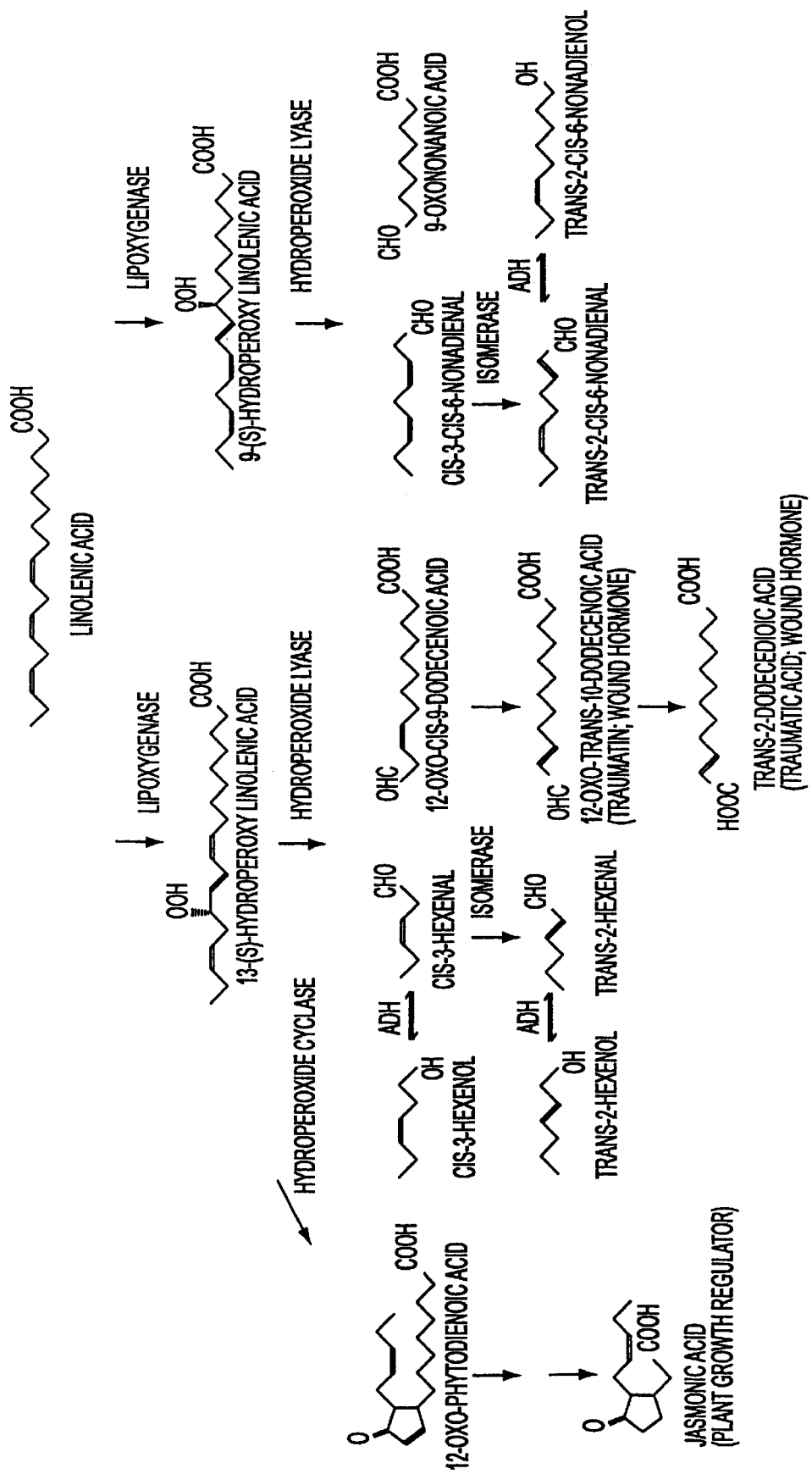
FIG. 1 summarizes schematically the degradation of linolenic acid by the lipoxygenase pathway in plants FIG. 2 summarizes schematically the formation of cis-3-hexenol from 13-(S)-hydroperoxy linolenic acid by recombinant HPO lyase protein and alcohol dehydrogenase.
Figure 2:
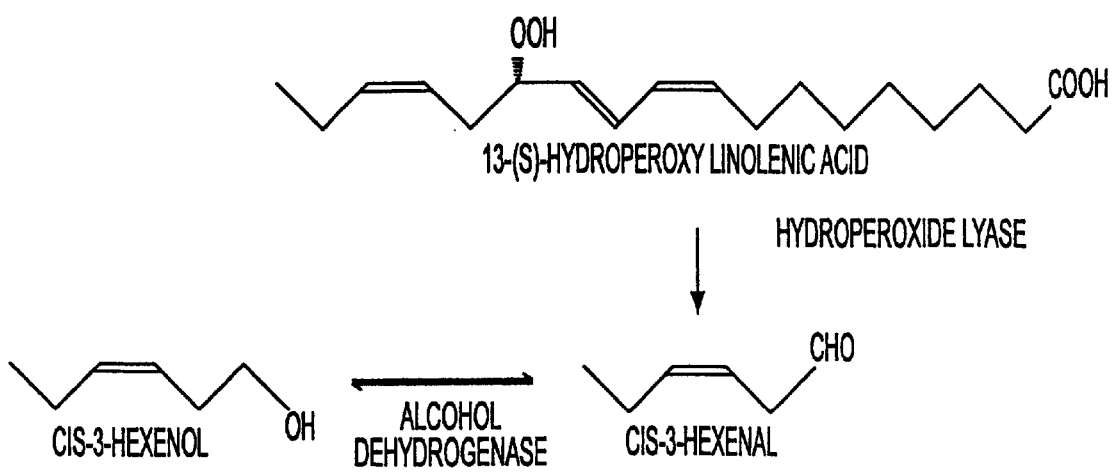

Linolenic acid-(13S)-hydroperoxide was produced as described by Iacazio et al. (J. Org. Chem. 55, 1690–1691

[1990]) using Lipoxygenase-1 from Fluka (62340; Fluka, Buchs, Switzerland). Linolenic acid (62159; Fluka, Buchs, Switzerland) was used as precursor. Typically, a 60–70 mM aqueous solution of linolenic acid hydroperoxide was obtained under these conditions. This precursor can be stored for several month in 0.5 ml aliquots at −80° C.

Enzyme activity of banana HPO lyase protein was measured as follows: The reaction volume was 500 µl containing 20 mM sodium phosphate buffer, pH 6.8, 0.8 mM linolenic acid hydroperoxide and 50 µl of banana HPO lyase protein in aqueous buffer. The reaction was incubated for 10 min at room temperature and subsequently stopped by the addition of 200 µl of methyl-t-butylether containing an internal standard such as cis-3-hexenol. Activity of the lyase was determined as function of the amount of cis-3-hexenal produced during this standard reaction. Cis-3-hexenal was quantified by capillary gaschromatography as described by Olias et al., J. Agric. Food Chem. Vol. 41, 2368–2373 (1993).

EXAMPLE 1

Purification of Banana HPO Lyase Protein

About 5 kg of banana (Musa sp.; purchased from a local store) tissue was used for the isolation of the HPO lyase protein. Operations were carried out at 4° C. Aliquots of 560 g of banana tissue were homogenized in 1.1 l of ice cold buffer A (50 mM sodium phosphate buffer, pH 6.8, 2 mM dithiothreitol, 7 mM EDTA, 0.25 mM PMSF) and 36 g of PVP K30 from Fluka using a Warring blender. The homogenate was centrifuged at 10'000×g for 20 min and the supernatant (crude extract) was filtered through 3 layers of Miracloth (Calbiochem). The resulting filtrate was centrifuged at 100'000×g for 50 min and the pellet was homogenized and solubilized in 150 ml buffer B (20 mM Tris, pH 7.0, 0.1 % Triton X114) and subsequently clarified by centrifugation at 100'000×g for 30 min. The solubilized HPO lyase protein fraction was applied to a column of DEAE-CL6B (2.6 cm i.d.×20 cm; Pharmacia) that was equilibrated with buffer A. HPO lyase protein was eluted with a linear gradient of 0–0.5 M ammonium acetate in buffer B at 2 ml/min. Fractions were collected and screened for activity of HPO lyase. Active fractions were pooled and concentrated by ultrafiltration with an Amicon ultrafiltration unit containing a PM30 membrane (Amicon). The concentrate, about 8 ml, was applied in 2 ml aliquots per chromatography run to a gelfiltration column (Superose 6, 23 mm i.d.×50 cm, attached to a FPLC apparatus, Pharmacia). The flow rate was 1.5 ml/min of buffer B and fractions were collected and assayed for activity of HPO lyase. Active fractions were pooled and applied to an anion exchange chromatography (Poros 20 HQ, 4.6 mm i.d.×100 mm, Perceptive Biosystems). The chromatography was performed on a BioCAD-Sprint workstation (Perseptive Biosytems) with a flow rate of 5 ml/min. The HPO lyase was eluted with a linear gradient of buffer C (20 mM Tris, pH 7.0, 0.2% Triton X100 reduced) to buffer C containing 0.5 M ammonium acetate. Fractions were collected and assayed for HPO lyase activity. Active fractions were pooled, the pH was set to approximately 7.5 by dilution with buffer D (20 mM Tris pH 8.0, 0.2% Triton X100 reduced) and reapplied to the Poros anion exchange column equilibrated with buffer D. The HPO lyase activity was eluted with a gradient of 0–0.4 M ammonium acetate in buffer D. Fractions were collected, assayed for HPO lyase activity and aliquots of each were analysed by SDS-polyacrylamide gel electrophoresis (SDS-PAGE). SDS-PAGE was performed as described by Ausubel et al., eds. "Current Protocols in Molecular Biology", (1995) published by Current Protocols, USA, using a Minigel apparatus (Hoeffer SE280). The gel was stained using a silver stain Plus kit (Bio-Rad) according to the manufacturers instructions. The HPO lyase was detected as protein band of about 55 kDA size. The specific activity was 6000 µmol cis-3-hexenal produced/hr/mg of protein. The protein activity was purified to more than 9000-fold.

Fractions containing the activity maxima from all repetitive purification runs were pooled and concentrated by precipitation. For this, the pooled fractions were mixed with two volumes of ethanol and cooled to −20° C. for 5 hrs. The mixture was centrifuged at 20'000×g for 30 min and the resulting pellet was washed with 70% ethanol and air-dried for 15 min. The pellet was resuspended in 160 µl Tricine sample buffer (Novex, San Diego, USA) and the sample subjected to SDS-Tricine-PAGE (10–20%) (Novex, San Diego, USA). The protein bands were blotted onto a PVDF membrane (Immobilon PSQ, Millipore) with transfer buffer (10 mM 3-(cyclohexylamino)-1-propanesulfonic acid, 10% methanol, pH 11.0) for 60 min at 400 mA in a Trans-Blot cell (BioRad Laboratories, Richmond, Calif.) and stained with Ponceau S (0.1% Ponceau S in 10% acetic acid). The stained bands were cut out of the gel and digested in 100 mM Tris-HCl, pH 8.0, containing 1% reduced Triton X-100 (RTIX), 10% acetonitrile and 1 µg Lys-C overnight at 37° C. The samples were loaded on a Vydac C8 (250×1 mm) reverse-phase column. Sequence analysis of the eluted peptides was performed on a ABI Procise Protein Sequencer.

Amino acid sequences were obtained from 4 individual peptides as shown below
PEP1: WLALQLLPTVK (SEQ ID NO:3)
PEP2: SIIGADPSVSPDVGENGFVMLD (SEQ ID NO:4)
PEP3: NILIGDYMPSLSFTGDTRVVVYLDP (SEQ ID NO:5)
PEP4: (D)GLDRF(N)FQGPETFFRSRMAT(H) (SEQ ID NO:6)
(amino acid residues in parentheses are only tentatively assigned)

EXAMPLE 2

Cloning of DNA Encoding HPO Lyase Protein

A. Isolation of RNA from banana leaves

Banana (Musa sp.) leaves containing high hydroperoxide lyase activity were frozen in liquid nitrogen and the tissue was powdered using mortar and pestle. Total RNA was isolated from the leaf powder using the RNeasy total RNA purification system from Qiagen according to the manufacturer's protocol supplied with the purification system. Poly A⁺mRNA was obtained from the total RNA obtained using an oligotex mRNA Kit purchased from Qiagen (Qiagen AG, 4052 Basel, Switzerland).

B. Generation of a HPO lyase probe

A number of degenerate PCR primers were designed based on. the amino acid sequences obtained from the HPO lyase peptides. Different primer pairs were used to amplify part of the banana HPO lyase gene. A specific amplification product was obtained, using the following sense and antisense primer pair:

```
sense:     5' TTT CAA GGI CCI GAA ACI TTT TT 3' (SEQ ID NO:7)
               C   G           G       C
```

```
antisense: 5' GG CAT ATA ATC ICC IAT IAA AAT 3' (SEQ ID NO:8)
                 G   G           G G
                                 T
```

(multiple nucleotides at a single position reflect the degeneracy, equal amount of each nucleotide were incorporated into that position, I designates Inosine)

First strand cDNA synthesis was carried on about 100 ng of total RNA using SuperScript RNase H-Reverse Transkriptase (Gibco BRL). PCR with AmpliTaq (Perkin-Elmer) on the cDNA was performed for 40 cycles (initial heating 94° C., 3 min, annealing 50° C., 1 min, extension 72° C., 1.5 min, denaturation 94° 0.5 min; GeneAmp PCR System 2000, Perkin Elmer).

The approximately 200 bp PCR product was isolated from an agarose gel and cloned into the pCR-Script SK(+) vector (Stratagene). The DNA sequence of the gene fragment was determined (commercial service: Microsynth GmbH, Balgach, Switzerland). The amino acid sequence encoded by the gene fragment is as follows:

```
                                              (SEQ ID NO:9)
FQGPETFFRS RMATHKSTVF RTNMPPTFPF FVGVDPRVVT

VLDCTSFSAL FDLEVVEKKN ILIGDYMP
```

This gene fragment was used to generate a radioactive probe. For this, 50 ng of gel-purified fragment were labeled using the BioPrime DNA labeling System (GibcoBRL) essentially as described by the manufacturer. Instead of using biotinylated nucleotides, [α32P] dCTP (50 μCi, 6000 Ci/mmol; Amersham) was used. Nonincorporated nucleotides were removed using the QIAquick Spin PCR purification kit (Qiagen).

C. Construction of a banana leaf cDNA library

3–5 μg of banana plant mRNA were used to prepare cDNA which was then ligated into λZAP Express™ vector using the ZAP Express™ cDNA Gigapack II Gold cloning kit (Stratagene GmbH, Heidelberg, Germany). The phages obtained were then amplified before initial screening of the gene bank.

D. Screening of the banana leaf cDNA library

About 6×10⁵ plaques were screened using the radioactive HPO lyase gene fragment (see above). Hybridization was done using the Quickhybe solution from Stratagene and 100 μg/ml salmon sperm DNA for 3 hrs at 68° C. Two rounds of screening were carried out. A total of 18 positive clones were obtained. The lambda vector containing the positive inserts were converted into phagemids using ExAssist Helper Phages as described (ZAP-cDNA® II Gold cloning kit, Stratagene) and plasmid DNA was isolated from all clones using the Plasmid Midi Kit (Qiagen) according to the manufacturers description.

E. DNA sequence determination of the HPO lyase gene from banana

The DNA sequence of the phagemid insert was determined at a commercial sequencing center (MediGene GmbH, Martinsried, Germany) and is given as SEQ ID No:1.

EXAMPLE 3

Expression of HPO Lyase Protein in Yeast

A. Subcloning of the cDNA into the yeast expression vector pYX233

The cDNA insert of the phagemid obtained as described above was subcloned into yeast expression vector pYX233 (R&D systems, Abingdon, UK). For this purpose oligonucleotides with one part corresponding to the C-, respectively N-terminal sequence of the cDNA and the second part harboring an appropriate restriction site recognition sequence were used. The two following oligonucleotides were synthesized (Microsynth GmbH, Balgach, Switzerland):

sense: 5' CATGCCATGGCTATGATGTGGTCG 3'(SEQ ID NO:10)

antisense: 5' GAGAAGCTTGAGCTCTAGCCTCCTGCAACGTC 3-(SEQ ID NO:11)

Using these 2 primers a PCR reaction was carried out on 10 ng Phagemid using AmpliTAQ (Perkin-Elmer) for 25 cycles with conditions as given in example 2. The 1.6 kb PCR-product was digested with the restriction enzymes Ncol and Sacl (New England Biolabs Inc.). The double digested PCR product was then purified and isolated from agarose gels using the QiaEx Kit (Qiagen). In parallel, the yeast expression vector pYX233 was linearized by digestion with Ncol and Sacl. The open vector and the purified PCR product were ligated in a 1:1 molar amount according to standard protocoll as reported by Sambrook et al., supra. The plasmid now containing the cDNA was transformed into E. coli DH5α (GibcoBRL) from which the plasmid DNA was isolated using Qiagen Plasmid Midi Kit (Qiagen, Germany).

B. Transformation of yeast strain

5 μg of the plasmid was transformed into S. cerevisiae DBY746 (ATCC 44773) as described by Klebe et al., supra. The transformed yeast cells were plated onto suitable selective media (SD medium supplemented with the amino acids histidine, leucine, uracil; see Sherman in "Guide to yeast genetics and molecular biology", Guthrie and Fink, eds., Methods in Enzymology, Academic Press, Inc., Vol. 194, 3–21 (1991) for description of the medium) and grown for 4 days at 30° C. These cells were the source for the heterologous lyase protein. Colonies grown on the selective agar media were grown in liquid SD medium supplemented with the above amino acids.

Induction of expression of the gene encoding the lyase protein was achieved by addition of 2% (final concentration) of galactose to the growth medium when culture densities had reached an absorption of 0.4 measured at 600 nm. The induction protocol was performed essentially as described by Mylin et al. in "Gene expression technology", Goeddel, ed., Methods in Enzymology, Academic Press, Inc., Vol. 185, 297–308 (1991). Culture samples were removed 4 hr after addition of galactose and the activity of the lyase protein was measured from broken cells as described before.

EXAMPLE 4
Production of Cis-3-hexenol

S. cerevisiae cells containing the recombinant plasmid, vector pYX233 containing the HPO lyase gene as described in example 3, were cultured in 100 ml SD medium supplemented with the amino acids histidine, leucine, uracil (see Sherman, supra, for description of the medium) at 30° C. Induction conditions were as described in example 3.

The cells were harvested by centrifugation (8000×g for 10 min) and the cell pellet was resuspended in 10 ml of 10 mM phosphate buffer, pH 6.8, 0.05% Triton-X100, 0.25 mM PMSF, 1 mM linolenic acid hydroperoxide. To the cell suspension, 10 g glass beads (0.2–0.4 mm in diameter; Sigma) were added, and the mixture was vigorously vortexed 3 times for 1 min. The reaction mixture was incubated for 30 min at room temperature, after which 0.2 g bakers yeast cells (Hefe Schweiz AG) were added. The incubation was carried out for an additional 30 min.

The reaction mixture was extracted with 10 ml of methyl-t-butylether and the organic phase separated by centrifugation (8000×g for 10 min). The supernatant containing the produced cis-3-hexenol was saved. Cis-3-hexenol concentration was determined by capillary gas chromatography as described by Olias et al. (1993) J. Agric. Food Chem. 41, 2368–2373.

EXAMPLE 5
Production of Cis-3-hexenol and Cis-3-hexenal Using Whole Yeast Cells The lyase gene was cloned into the yeast expression vector pYX212 (R&D Systems). For this, the double digested and purified PCR product (as described in Example 3) was ligated into the vector pYX212 which was linearized with the restriction enzymes NcoI and SacI. The plasmid which contained the PCR product was transformed into *E. coli* DH5a (Gibco BRL; Sambrook et al., supra) from which the plasmid DNA was isolated using Qiagen Plasmid Midi Kit (Qiagen, Germany). 5 μg of the plasmid was transformed into *S. cerevisiae* DBY746 (ATCC 44773) as described by Klebe et al., supra. The transformed yeast cells were plated onto suitable selective media (SD medium supplemented with the amino acids histidine, leucine, tryptophane; see Sherman, supra, for description of the medium) and grown for 4 days at 30° C. Colonies grown on the selective agar media were regrown in liquid SD medium supplemented with the above amino acids.

Production of Cis-3-hexenal

S. cerevisiae cells containing the recombinant plasmid, vector pYX212 containing the HPO lyase gene as described above, were cultured in 100 ml SD medium supplemented with the above amino acids at 30° C. until culture densities reached an absorption of about 10 measured at 600 nm. The HPO lyase was expressed continuously from the constitutive triosephosphate isomerase promoter from the vector pYX212. The cells were harvested by centrifugation (8000×g for 10 min) and resuspended in 20 ml 10 mM phosphate buffer, pH 6.8, 10 mM linolenic acid hydroperoxide. The reaction mixture was incubated for 30 min at room temperature and subsequently extracted with 10 ml of methyl-t-butylether. The organic phase was separated by centrifugation (8000×g for 10 min) and the supernatant containing the produced cis-3-hexenal was saved.

Production of Cis-3-hexenol

S. cerevisiae cells containing the recombinant plasmid, vector pYX212 containing the HPO lyase gene as described above, were cultured in 100 ml SD medium supplemented with the above amino acids at 30° C. until culture densities reached an absorption of about 10 measured at 600 nm. The HPO lyase was expressed continuously from the constitutive triosephosphate isomerase promoter from the vector pYX212. The cells were harvested by centrifugation (8000×g for 10 min) and resuspended in 20 ml 10 mM phosphate buffer, pH 6.8, 10 mM linolenic acid hydroperoxide. 2 ml of ethanol and 10 g of commercial bakers yeast cells (Hefe Schweiz AG) were added to the resuspended recombinant yeast cells. The reaction mixture was incubated for 30 min at room temperature and subsequently extracted with 10 ml of methyl-t-butylether. The organic phase was separated by centrifugation (8000×g for 10 min) and the supernatant containing the produced cis-3-hexenol was saved. Cis-3-hexenal and cis-3-hexenol concentrations were determined as described in Example 4.

---

What is claimed is:

1. A process for the production of green note compounds, which process comprises the steps of:
   (a) incubating a host cell comprising a DNA encoding SEQ ID NO:2 or a fragment thereof having hydroperoxide lyase activity with fatty acid hydroperoxide; and
   (b) incubating the resulting aliphatic aldehyde with a reactant selected from the group consisting of isomerase and alcohol dehydrogenase.

2. A process for producing cis-3-hexenol, which process comprises the steps of:
   (a) incubating a host cell comprising a DNA encoding SEQ ID NO:2 or a fragment thereof having hydroperoxide lyase activity with 13-(S)-hydroperoxide linolenic acid; and
   (b) reducing the resulting cis-3-hexenal with alcohol dehydrogenase.

* * * * *

SEQUENCE LISTING

```
<160> NUMBER OF SEQ ID NOS: 11

<210> SEQ ID NO 1
<211> LENGTH: 1638
<212> TYPE: DNA
<213> ORGANISM: Musa sp.
<220> FEATURE:
<221> NAME/KEY: CDS
<222> LOCATION: (25)..(1473)

<400> SEQUENCE: 1
aagaagaaga gagggaaggt acgg atg gct atg atg tgg tcg tca gcc tcc        51
                         Met Ala Met Met Trp Ser Ser Ala Ser
                          1               5 gcc acc gcc gtc acc acg ctg ccg acg agg ccc atc cct gga agc tac        99
Ala Thr Ala Val Thr Thr Leu Pro Thr Arg Pro Ile Pro Gly Ser Tyr
 10              15                  20                  25 ggc ccg ccg ctg gtg ggc ccc ctc aag gac cgc ctc gac tac ttc tgg      147
Gly Pro Pro Leu Val Gly Pro Leu Lys Asp Arg Leu Asp Tyr Phe Trp
             30                  35                  40
```

-continued

| | |
|---|---|
| ttt cag gga ccg gag acc ttc ttc cgc agc cgg atg gcc acc cac aag<br>Phe Gln Gly Pro Glu Thr Phe Phe Arg Ser Arg Met Ala Thr His Lys<br>                     45                            50                       55 | 195 |
| agc acc gtg ttc cgc acc aac atg ccc ccc acc ttc ccc ttc ttc gtt<br>Ser Thr Val Phe Arg Thr Asn Met Pro Pro Thr Phe Pro Phe Phe Val<br>           60                       65                      70 | 243 |
| gga gtc gac ccc cgc gtg gtc acc gtc ctc gac tgc aca tcc ttc tcc<br>Gly Val Asp Pro Arg Val Val Thr Val Leu Asp Cys Thr Ser Phe Ser<br>75                       80                       85 | 291 |
| gcc ctc ttc gac ctc gag gtc gtg gag aag aag aac att ctc atc ggg<br>Ala Leu Phe Asp Leu Glu Val Val Glu Lys Lys Asn Ile Leu Ile Gly<br>90                       95                     100              105 | 339 |
| gac tac atg ccc agc ctc agc ttc acc ggc gac acc cgc gtc gtc gtg<br>Asp Tyr Met Pro Ser Leu Ser Phe Thr Gly Asp Thr Arg Val Val Val<br>                110                      115                     120 | 387 |
| tac ctc gac ccc tcc gag ccc gac cac gcc cgc gtg aag agc ttc tgc<br>Tyr Leu Asp Pro Ser Glu Pro Asp His Ala Arg Val Lys Ser Phe Cys<br>                125                      130                     135 | 435 |
| ttg gaa ctc ctc agg cgc ggc gcc aag acc tgg gtc tcc tcg ttc ctc<br>Leu Glu Leu Leu Arg Arg Gly Ala Lys Thr Trp Val Ser Ser Phe Leu<br>           140                      145                     150 | 483 |
| tcc aat ctc gat gtc atg ctc gcc acc ata gag cag ggg atc gcc aag<br>Ser Asn Leu Asp Val Met Leu Ala Thr Ile Glu Gln Gly Ile Ala Lys<br>           155                      160                     165 | 531 |
| gat ggc tcc gcc ggc tta ttc ggc ccg ctg cag aag tgc atc ttc gcg<br>Asp Gly Ser Ala Gly Leu Phe Gly Pro Leu Gln Lys Cys Ile Phe Ala<br>170                      175                      180                185 | 579 |
| ttc ctc tgc aag agc atc atc ggg gcc gac ccg tcg gtg tcg ccc gac<br>Phe Leu Cys Lys Ser Ile Ile Gly Ala Asp Pro Ser Val Ser Pro Asp<br>                190                      195                     200 | 627 |
| gtg gga gaa aat ggc ttc gtc atg ctc gac aag tgg ctt gcg ctg cag<br>Val Gly Glu Asn Gly Phe Val Met Leu Asp Lys Trp Leu Ala Leu Gln<br>           205                      210                     215 | 675 |
| ctc ctc ccg acg gtg aag gtc ggg gcc atc ccg caa ccc ctg gag gag<br>Leu Leu Pro Thr Val Lys Val Gly Ala Ile Pro Gln Pro Leu Glu Glu<br>           220                      225                     230 | 723 |
| atc ctc ctc cac tcc ttc ccc ctc ccc ttc ttc ctc gtg agc cgc gat<br>Ile Leu Leu His Ser Phe Pro Leu Pro Phe Phe Leu Val Ser Arg Asp<br>235                      240                      245 | 771 |
| tac cgg aag ctg tac gaa ttc gtc gag aag caa ggc caa gag gtt gtc<br>Tyr Arg Lys Leu Tyr Glu Phe Val Glu Lys Gln Gly Gln Glu Val Val<br>250                      255                      260                265 | 819 |
| cgg cga gcg gaa acc gag cac ggg ctc agc aag cac gac gcc atc aac<br>Arg Arg Ala Glu Thr Glu His Gly Leu Ser Lys His Asp Ala Ile Asn<br>                270                      275                     280 | 867 |
| aac atc ttg ttc gtc cta gga ttc aac gcc ttc ggc ggc ttc tcg gtc<br>Asn Ile Leu Phe Val Leu Gly Phe Asn Ala Phe Gly Gly Phe Ser Val<br>           285                      290                     295 | 915 |
| ttc ttc ccc acg ctc ctg acc acc ata ggg agg gac aag acg ggc ctg<br>Phe Phe Pro Thr Leu Leu Thr Thr Ile Gly Arg Asp Lys Thr Gly Leu<br>           300                      305                     310 | 963 |
| cgg gag aag ctc aag gac gag gtg cgc agg gtc atg aag agt aga ggg<br>Arg Glu Lys Leu Lys Asp Glu Val Arg Arg Val Met Lys Ser Arg Gly<br>315                      320                      325 | 1011 |
| gag aag cgg ccg agc ttc gag acg gtg cgg gag atg gag ctg gtg cga<br>Glu Lys Arg Pro Ser Phe Glu Thr Val Arg Glu Met Glu Leu Val Arg<br>330                      335                      340                345 | 1059 |
| tcg acg gtg tac gag gtc ctg cgg ctg aac ccg ccg gtg ccg ctg cag<br>Ser Thr Val Tyr Glu Val Leu Arg Leu Asn Pro Pro Val Pro Leu Gln<br>                350                      355                     360 | 1107 |

-continued

```
tac ggg cgg gcg cgc acc gac ttc acg ctg aac tcc cac gac gcg gcg    1155
Tyr Gly Arg Ala Arg Thr Asp Phe Thr Leu Asn Ser His Asp Ala Ala
            365                 370                 375 ttc aag gtt gag aag ggg gag ttg ctg tgc ggg tac cag ccg ctg gtg    1203
Phe Lys Val Glu Lys Gly Glu Leu Leu Cys Gly Tyr Gln Pro Leu Val
            380                 385                 390 atg cgg gat cca gcg gtg ttc gac gac ccg gag acg ttc gcc ccg gaa    1251
Met Arg Asp Pro Ala Val Phe Asp Asp Pro Glu Thr Phe Ala Pro Glu
        395                 400                 405 agg ttc atg ggc agc ggg aag gag ctg ctc aag tac gtc ttc tgg tcc    1299
Arg Phe Met Gly Ser Gly Lys Glu Leu Leu Lys Tyr Val Phe Trp Ser
410                 415                 420                 425 aac ggg ccg gag acg ggt acg ccg acg ccg gcc aac aag cag tgc gcc    1347
Asn Gly Pro Glu Thr Gly Thr Pro Thr Pro Ala Asn Lys Gln Cys Ala
                430                 435                 440 gcg aag gac tac gtg gtg gag acg gcg tgc ctg ctg atg gcg gag atc    1395
Ala Lys Asp Tyr Val Val Glu Thr Ala Cys Leu Leu Met Ala Glu Ile
                445                 450                 455 ttc tac cgc tac gac gag ttc gtg tgc gcc gac gac gcc atc tcc gtg    1443
Phe Tyr Arg Tyr Asp Glu Phe Val Cys Ala Asp Asp Ala Ile Ser Val
            460                 465                 470 acg aag ctg gat aga gcg aga gaa tgg gag taaacggtat tcaagtcgga      1493
Thr Lys Leu Asp Arg Ala Arg Glu Trp Glu
        475                 480 agcgacataa ggagacggcc aactccaccg ttgctaattc aagtcgtact ccaaatcggt  1553
attcatatca tcgttccatt ggggtgatga agagataaat aaaatttgac gttgcaggag  1613
gctacaaaaa aaaaaaaaaa aaaaa                                        1638

<210> SEQ ID NO 2
<211> LENGTH: 483
<212> TYPE: PRT
<213> ORGANISM: Musa sp.

<400> SEQUENCE: 2

Met Ala Met Met Trp Ser Ser Ala Ser Ala Thr Ala Val Thr Thr Leu
1               5                   10                  15

Pro Thr Arg Pro Ile Pro Gly Ser Tyr Gly Pro Pro Leu Val Gly Pro
            20                  25                  30

Leu Lys Asp Arg Leu Asp Tyr Phe Trp Phe Gln Gly Pro Glu Thr Phe
        35                  40                  45

Phe Arg Ser Arg Met Ala Thr His Lys Ser Thr Val Phe Arg Thr Asn
    50                  55                  60

Met Pro Pro Thr Phe Pro Phe Val Gly Val Asp Pro Arg Val Val
65                  70                  75                  80

Thr Val Leu Asp Cys Thr Ser Phe Ser Ala Leu Phe Asp Leu Glu Val
                85                  90                  95

Val Glu Lys Lys Asn Ile Leu Ile Gly Asp Tyr Met Pro Ser Leu Ser
            100                 105                 110

Phe Thr Gly Asp Thr Arg Val Val Tyr Leu Asp Pro Ser Glu Pro
        115                 120                 125

Asp His Ala Arg Val Lys Ser Phe Cys Leu Glu Leu Leu Arg Arg Gly
    130                 135                 140

Ala Lys Thr Trp Val Ser Ser Phe Leu Ser Asn Leu Asp Val Met Leu
145                 150                 155                 160

Ala Thr Ile Glu Gln Gly Ile Ala Lys Asp Gly Ser Ala Gly Leu Phe
                165                 170                 175
```

Gly Pro Leu Gln Lys Cys Ile Phe Ala Phe Leu Cys Lys Ser Ile Ile
            180                 185                 190

Gly Ala Asp Pro Ser Val Ser Pro Asp Val Gly Glu Asn Gly Phe Val
        195                 200                 205

Met Leu Asp Lys Trp Leu Ala Leu Gln Leu Leu Pro Thr Val Lys Val
    210                 215                 220

Gly Ala Ile Pro Gln Pro Leu Glu Glu Ile Leu Leu His Ser Phe Pro
225                 230                 235                 240

Leu Pro Phe Phe Leu Val Ser Arg Asp Tyr Arg Lys Leu Tyr Glu Phe
                245                 250                 255

Val Glu Lys Gln Gly Gln Glu Val Val Arg Arg Ala Glu Thr Glu His
            260                 265                 270

Gly Leu Ser Lys His Asp Ala Ile Asn Asn Ile Leu Phe Val Leu Gly
        275                 280                 285

Phe Asn Ala Phe Gly Gly Phe Ser Val Phe Phe Pro Thr Leu Leu Thr
    290                 295                 300

Thr Ile Gly Arg Asp Lys Thr Gly Leu Arg Glu Lys Leu Lys Asp Glu
305                 310                 315                 320

Val Arg Arg Val Met Lys Ser Arg Gly Glu Lys Arg Pro Ser Phe Glu
                325                 330                 335

Thr Val Arg Glu Met Glu Leu Val Arg Ser Thr Val Tyr Glu Val Leu
            340                 345                 350

Arg Leu Asn Pro Pro Val Pro Leu Gln Tyr Gly Arg Ala Arg Thr Asp
        355                 360                 365

Phe Thr Leu Asn Ser His Asp Ala Ala Phe Lys Val Glu Lys Gly Glu
    370                 375                 380

Leu Leu Cys Gly Tyr Gln Pro Leu Val Met Arg Asp Pro Ala Val Phe
385                 390                 395                 400

Asp Asp Pro Glu Thr Phe Ala Pro Glu Arg Phe Met Gly Ser Gly Lys
                405                 410                 415

Glu Leu Leu Lys Tyr Val Phe Trp Ser Asn Gly Pro Glu Thr Gly Thr
            420                 425                 430

Pro Thr Pro Ala Asn Lys Gln Cys Ala Ala Lys Asp Tyr Val Val Glu
        435                 440                 445

Thr Ala Cys Leu Leu Met Ala Glu Ile Phe Tyr Arg Tyr Asp Glu Phe
    450                 455                 460

Val Cys Ala Asp Asp Ala Ile Ser Val Thr Lys Leu Asp Arg Ala Arg
465                 470                 475                 480

Glu Trp Glu

<210> SEQ ID NO 3
<211> LENGTH: 11
<212> TYPE: PRT
<213> ORGANISM: Musa sp.

<400> SEQUENCE: 3

Trp Leu Ala Leu Gln Leu Leu Pro Thr Val Lys
 1               5                  10

<210> SEQ ID NO 4
<211> LENGTH: 22
<212> TYPE: PRT
<213> ORGANISM: Musa sp.

<400> SEQUENCE: 4

```
Ser Ile Ile Gly Ala Asp Pro Ser Val Ser Pro Asp Val Gly Glu Asn
 1               5                  10                  15

Gly Phe Val Met Leu Asp
             20

<210> SEQ ID NO 5
<211> LENGTH: 25
<212> TYPE: PRT
<213> ORGANISM: Musa sp.

<400> SEQUENCE: 5

Asn Ile Leu Ile Gly Asp Tyr Met Pro Ser Leu Ser Phe Thr Gly Asp
 1               5                  10                  15

Thr Arg Val Val Val Tyr Leu Asp Pro
             20                  25

<210> SEQ ID NO 6
<211> LENGTH: 22
<212> TYPE: PRT
<213> ORGANISM: Musa sp.
<220> FEATURE:
<221> NAME/KEY: UNSURE
<222> LOCATION: (1)
<223> OTHER INFORMATION: tentatively Aspartic acid (D)
<220> FEATURE:
<221> NAME/KEY: UNSURE
<222> LOCATION: (7)
<223> OTHER INFORMATION: tentatively Asparagine (N)
<220> FEATURE:
<221> NAME/KEY: UNSURE
<222> LOCATION: (22)
<223> OTHER INFORMATION: tentatively Histidine

<400> SEQUENCE: 6

Xaa Gly Leu Asp Arg Phe Xaa Phe Gln Gly Pro Glu Thr Phe Phe Arg
 1               5                  10                  15

Ser Arg Met Ala Thr Xaa
             20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Degenerate
      PCR primer (sense)  designed based on the amino acid sequences
      obtained from the HPO lyase peptides.
<220> FEATURE:
<221> NAME/KEY: unsure
<222> LOCATION: (3)
<223> OTHER INFORMATION: T or C
<220> FEATURE:
<221> NAME/KEY: unsure
<222> LOCATION: (6)
<223> OTHER INFORMATION: A or G
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: unsure
<222> LOCATION: (15)
<223> OTHER INFORMATION: A or G
<220> FEATURE:
<221> NAME/KEY: modified_base
<222> LOCATION: (18)
<223> OTHER INFORMATION: i
```

```
<220> FEATURE:
<221> NAME/KEY: unsure
<222> LOCATION: (21)
<223> OTHER INFORMATION: T or C

<400> SEQUENCE: 7
ttncanggnc nganacnttn ntt                                              23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Degenerate
      PCR primer (antisense) designed based on the amino acid sequences
      obtained from the HPO lyase peptides.
<220> FEATURE:
<221> NAME/KEY: unsure
<222> LOCATION: (6)
<223> OTHER INFORMATION: A or G
<220> FEATURE:
<221> NAME/KEY: unsure
<222> LOCATION: (9)
<223> OTHER INFORMATION: A or G
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (18)
<223> OTHER INFORMATION: i
<220> FEATURE:
<221> NAME/KEY: unsure
<222> LOCATION: (20)
<223> OTHER INFORMATION: A or G
<220> FEATURE:
<221> NAME/KEY: unsure
<222> LOCATION: (21)
<223> OTHER INFORMATION: A or G or T

<400> SEQUENCE: 8
ggcatntant cnccnatnan nat                                              23

<210> SEQ ID NO 9
<211> LENGTH: 68
<212> TYPE: PRT
<213> ORGANISM: Artificial Sequence
<220> FEATURE:
<223> OTHER INFORMATION: Description of Artificial Sequence: PCR product
      obtained from first strand cDNA synthesis using degenerate PCR
      primers.

<400> SEQUENCE: 9

Phe Gln Gly Pro Glu Thr Phe Phe Arg Ser Arg Met Ala Thr His Lys
 1               5                  10                  15

Ser Thr Val Phe Arg Thr Asn Met Pro Pro Thr Phe Pro Phe Phe Val
            20                  25                  30

Gly Val Asp Pro Arg Val Val Thr Val Leu Asp Cys Thr Ser Phe Ser
        35                  40                  45

Ala Leu Phe Asp Leu Glu Val Val Glu Lys Lys Asn Ile Leu Ile Gly
    50                  55                  60

Asp Tyr Met Pro
65
```

```
<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      oligonucleotide (sense) synthesized based on the C- and N-terminal
      sequence of the cDNA and containing a restriction site recognition
      sequence.

<400> SEQUENCE: 10
catgccatgg ctatgatgtg gtcg                                            24

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence:
      oligonucleotide (antisense) synthesized based on the C- and
      N-terminal sequence of the cDNA and containing a restriction site
      recognition sequence.

<400> SEQUENCE: 11
gagaagcttg agctctagcc tcctgcaacg tc                                   32
```